United States Patent [19]

Urban et al.

[11] Patent Number: 4,731,491

[45] Date of Patent: Mar. 15, 1988

[54] PROCESS FOR LIQUEFACTION OF LIGNIN

[75] Inventors: Peter Urban, Northbrook; Dusan J. Engel, Des Plaines, both of Ill.

[73] Assignee: UOP Inc., Des Plaines, Ill.

[21] Appl. No.: 821,190

[22] Filed: Jan. 22, 1986

[51] Int. Cl.$^4$ .................. C08H 15/02; C07C 37/00
[52] U.S. Cl. ..................... 568/761; 530/502; 530/503; 568/716; 568/799
[58] Field of Search ............... 530/502, 503; 568/716, 568/761, 799

[56] References Cited

U.S. PATENT DOCUMENTS

| 3,105,095 | 9/1963 | Oshima et al. | 530/503 X |
|---|---|---|---|
| 3,223,698 | 12/1965 | Oshima et al. | 530/503 |
| 3,253,044 | 5/1966 | Goheen | 530/503 X |
| 4,420,644 | 12/1983 | Huibers et al. | 568/799 X |
| 4,647,704 | 3/1987 | Engel et al. | 568/716 |

FOREIGN PATENT DOCUMENTS 700210 12/1964 Canada .

OTHER PUBLICATIONS

David W. Goheen, Lignin Structure and Reactions, American Chemical Society, Advances in Chemistry, Series No. 59.

Kirk-Othmer, "Encyclopedia of Chemical Technology", Third Edition, vol. 14, pp. 307-308 (J. Wiley and Sons Inc., 1980).

*Primary Examiner*—Earl Nielsen
*Attorney, Agent, or Firm*—Thomas K. McBride; John F. Spears, Jr.; Eugene I. Snyder

[57] ABSTRACT

Liquefaction of lignin by hydrogenolysis in the presence of a catalytic composition of metal sulfides which are prepared in situ and in the presence of a lower aliphatic alcohol affords substantially increased yields of monophenols. When methanol is used in the presence of a catalyst which is a mixture of the sulfides of divalent iron, copper, and tin the total monophenols can be as high as 65% with the total cresols being about 45%. Phenol, which is used as a liquefying solvent, can itself be formed in good yield when lignin tar is used as the liquefying solvent. This affords the opportunity of conducting the liquefaction in a continuous fashion using two stages of reaction.

21 Claims, 1 Drawing Figure

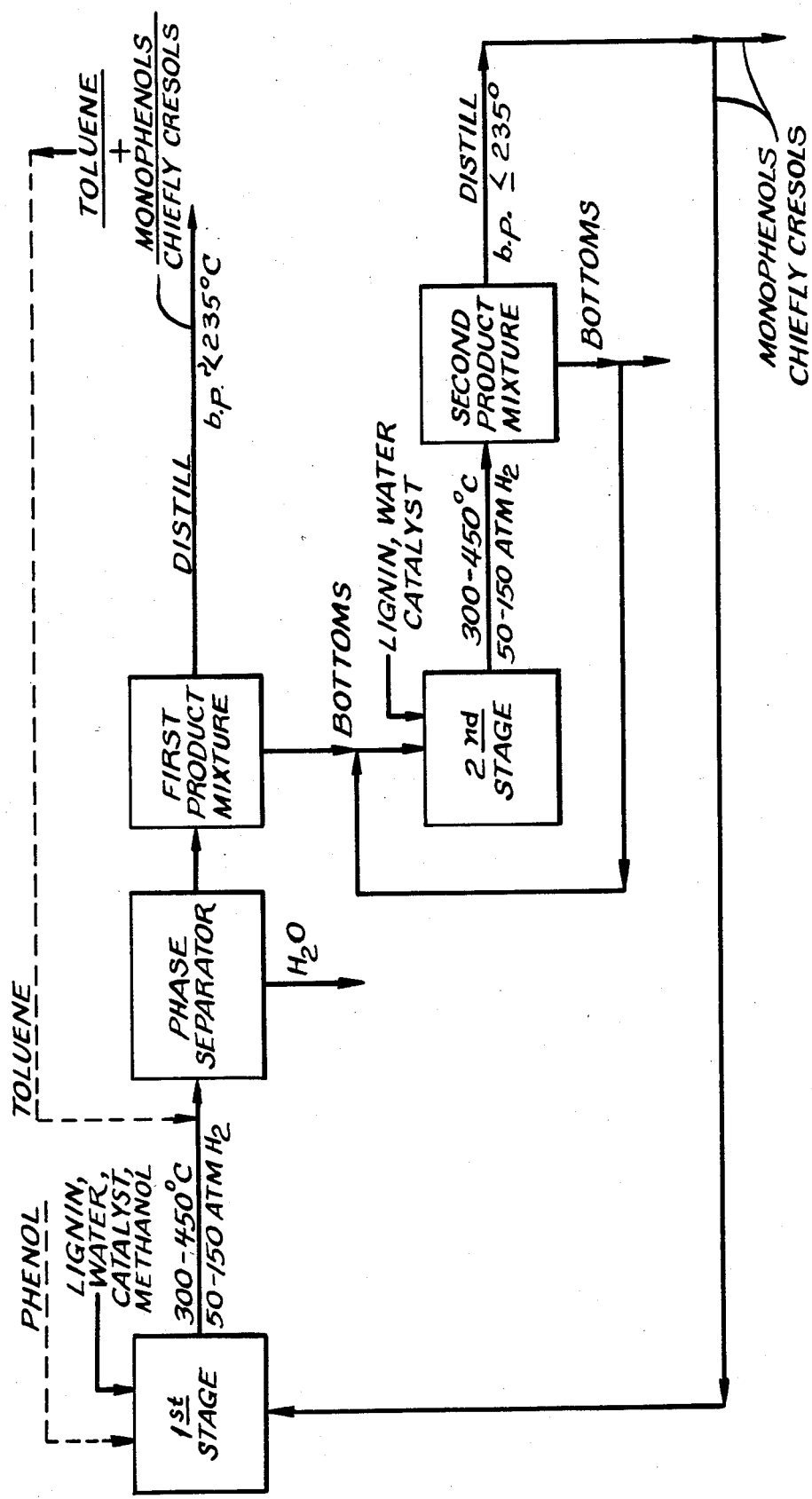

PROCESS FOR LIQUEFACTION OF LIGNIN

BACKGROUND OF THE INVENTION

Lignocellulosic materials represent a vast amount of renewable resources available in virtually every part of the world. The use of lignocellulosics as a raw material for chemicals continues to be limited by the nature of current delignification processes (i.e., separation of lignin from cellulosic and hemicellulosic components) and by the difficulty of converting the lignin obtained to articles of commerce. This application is directed toward the latter. More particularly, this application is directed to the hydrogenolysis of a species of lignin to afford phenols, especially cresols.

Catalytic hydrogenolysis of lignin was known for some time to effect liquefaction, but its utility was severely curtailed by its tendency to afford a product of little commercial value. With the advent of the so-called Noguchi process (Canadian Pat. No. 700,210) it was claimed that a mixture of $C_6$-$C_9$ monophenols would be obtained upon hydrogenolysis in yields as high as about 40%. The patentee used a catalyst of iron(II) sulfide with a co-catalyst of at least one sulfide of copper, silver, tin, cobalt, chromium, nickel, zinc, or molybdenum, and conducted the reaction in a solvent such as lignin tars and phenols at 250°–450° C. and an initial hydrogen pressure of 150–450 atmospheres. The process was extensively evaluated in a multitude of its variants, and although the high yields of monophenols as claimed by the patentee never could be reproduced the investigators concluded that the process remained the best one for lignin liquefaction to that date. David W. Goheen, Lignin Structure and Reactions, American Society, Advances in Chemistry Series, No. 59. However, another conclusion was that the process, even though the best one available, was economically unattractive because of the kind of lignin used, the relatively low economic value of the monophenol product mixture, and the loss of phenol itself when used as a solvent.

We have developed an improved and modified Noguchi process affording up to about 45% cresols and about 65% monophenols in the $C_6$-$C_9$ range, thus substantially improving the economic return of lignin liquefaction. Additionally, we have developed a process where lignin liquefaction is effected in two stages which can be coupled so as to afford a continuous or semicontinuous process. Our improvements leading to the processes which are our inventions herein are based on several discrete but interrelated observations.

One observation is that when the catalyst composition is prepared in situ the sulfides formed are purer than if independently prepared, stored, and then used. A result is that our catalyst tends to give somewhat higher yields of monophenols. Another observation is that alkali lignin from the Kraft process may be used as the lignin source, thereby eliminating any steps necessary for the conversion of such lignin to another form prior to its use as a feedstock for liquefaction. An observation which is the cornerstone of our invention is that if methanol, as representative of lower aliphatic alcohols, is used in the reaction mixture the cresol yields are increased substantially. This is particularly important since cresols are perhaps the source of maximum economic return from the liquefaction of lignin. The final observation leading to our invention is that when lignin tar is used as a phenol substitute in a second stage reaction phenol is formed in sufficient quantity that it can be recycled to the first stage whose monophenolic products are chiefly cresols. This makes possible a process where an external source of phenol is used in initial liquefaction, but thereafter can be generated in sufficient quantity as to provide for the continued needs of the liquefaction process.

DESCRIPTION OF THE FIGURE

The FIGURE depicts a process flow diagram of one embodiment for a continuous or semicontinuous two-stage lignin liquefaction.

SUMMARY OF THE INVENTION

The purpose of this invention is to provide for more efficient lignin liquefaction with improved economic return relative to the best prior procedure. An embodiment is the hydrogenolysis of alkali lignins from th Kraft process using a catalyst formed in situ and using phenol as a solvent in a partly aqueous reaction mixture containing a lower aliphatic alcohol. In a more specific embodiment the catalyst is formed by the addition of a sulfide source to an aqueous solution of divalent iron, copper, and tin salts. In a more specific embodiment the alcohol is methanol. In another embodiment the phenol is formed from lignin liquefaction in a second stage liquefaction where lignin tars are substituted as a solvent for phenol.

DESCRIPTION OF THE INVENTION

This invention is a method of liquefying lignin, especially that from the Kraft process, by forming in situ a catalyst composition resulting from the addition of a sulfide source to an aqueous solution containing divalent iron and soluble salts of a promoter selected from the group consisting of copper, tin, silver, chromium, cobalt, nickel, zinc, molybdenum, gallium, and germanium, and reacting a mixture of an aqueous solution of the lignin with phenol and a lower aliphatic alcohol in the presence of the catalyst in a hydrogen atmosphere under reaction conditions. When methanol is used as the lower aliphatic alcohol monophenols are formed in yields up to about 65% and total cresols are formed in a yield up to about 45%.

The lignin which is used as the feedstock in this invention is lignin from Kraft process of pulping. Such lignins are called alkali lignins and frequently will be referred to as alkali lignin hereafter. See Kirk-Othmer, "Encyclopedia of Chemical Technology," Third Edition, Volume 14, pages 307-8 (J. Wiley and Sons Inc., 1980). One useful property of such lignins utilized in the practice of this invention is their water solubility.

The catalytic composition used to liquefy lignin is a mixture of ferrous sulfide and smaller amounts of other metal sulfides as promoters. It is important that the catalytic composition be formed in situ, which is commonly done by adding a sulfide source to an aqueous solution of a water soluble divalent iron salt and a water soluble salt of one or more metals used as a promoter. Some useful promoters include copper, tin, silver, chromium, cobalt, nickel, zinc, molybdenum, gallium, and germanium, and a combination of copper(II) and tin(II) has been found to be especially effective. There is some preference for water soluble salts whose anions are those of strong acids, such as the halides, especially fluoride, chloride, and bromide, sulfates, nitrates, and phosphates. Any convenient sulfide source may be used, although alkali metal sulfides are most convenient.

The sulfides generally are added stoichiometrically so that no soluble metal remains in solution. That is, sulfide ususally is added in an amount sufficient to precipitate the metals present as their sulfides, although a small excess up to about 10% may be used. However, it should be clear that one can use less thn a stoichiometric amount although there is no reason to do so. The amount of iron in the catalytic composition calculated as iron(II) sulfide generally is from about 1% to about 10% by weight based on the lignin present. Promoters, especially copper and tin, are each present in the catalytic composition in from about 0.01 to about 0.5 molar proportion relative to iron, but usually are present in about 0.1 molar proportion.

To the aqueous mixture, whose pH generally is about 8, is added phenol, which is known to be an effective liquefying aid and solvent for the liquefaction of lignin. Between about 1 and about 5 parts by weight of phenol is used based on the lignin present. Although phenol acts as a solvent for lignin liquefaction, in our invention it also acts as a reactant under reaction conditions with lower saturated aliphatic alcohols.

The reaction mixture also contains lower saturated aliphatic alcohols, which is to say alcohols containing from 1 to about 4 carbonatoms. These alcohols include methanol, ethanol, n-propanol, i-propyl alcohol, n-butanol, i-butyl alcohol, s-butyl alcohol, and t-butyl alcohol, with methanol being the alcohol of choice. The alcohol is added at a level between about 5 and about 100 wt. % based on the lignin present, with the range between about 10% and 50% more frequently used. The alcohol acts as a co-reactant in lignin liquefaction by alkylating phenol under reaction conditions. Where methanol is used the cresols are formed in substantial amounts. Such alkylation is surprising since normally alkylation does not occur under alkaline conditions. At lower concentrations, which is to say between about 10 and about 20 wt. % based on the lignin present, there is a minimum loss of phenol with little change in the amount of cresol formed, and this is the preferred mode of operation.

The reaction is conducted in the presence of hydrogen at an elevated temperature. The temperature may range from about 300° to about 450° C. with the range between 375° to about 425° C. being favored. Hydrogen initially is present at a pressure from about 50 to about 150 atmospheres, which corresponds to about 1500 to approximately 5000 psi working pressure, and an initial hydrogen pressure between about 75 and 125 atmospheres is preferred.

Liquefaction normally is complete within a couple of hours, depending upon the reaction conditions employed. When the reaction is complete the reaction mixture usually is first separated from water with or without the addition of a solvent such as toluene, and then is flash evaporated with collection of distillate whose boiling point is under about 260° C. at atmospheric pressure. This fraction consists primarily of monophenols in the $C_6$ to $C_9$ range, and the mixture may be further separated if desired, for example, into the constituent cresols. The material which is not distilled is referred to as bottoms or lignin tars.

It has been observed that when lignin tars are used as a solvent with lignin in aqueous solution, hydrogenolysis in the presence of a catalyst affords phenol itself as the chief monophenolic product. Therefore, lignin tars can be used in a second stage of a process where phenol, which is used as the solvent in a first stage, is internally generated. This leads to the process depicted in the FIGURE.

In the first stage there is reacted a mixture of an aqueous solution of lignin from the Kraft process, phenol, and a lower aliphatic alcohol in the presence of a catalytic composition of sulfides of divalent iron, copper, and tin in a hydrogen atmosphere at a temperature between 300° and 450° C. and a pressure between about 50 and 150 atmospheres initially, essentially as previously described. One difference is that although a catalytic composition which is formed in situ is preferred, an equivalent mixture of metal sulfides which is independently prepared outside of the reaction mixture also can be utilized, but not necessarily with equivalent results.

When reaction in the first stage is complete substantially all the material corresponding to a boiling point less than about 235° C. at atmospheric pressure is recovered from the first product mixture. The remainder of the first product mixture is then used as a solvent, albeit probably a reactive one, with an aqueous solution of a lignin from the Kraft process in the presence of the catalytic composition as previously described in a hydrogen atmosphere under reaction conditions as previously cited. This is the second stage of reaction and affords a second product mixture which is then distilled. The distillate corresponding to a boiling point up to about 235° C. at atmospheric pressure is collected and found to consist of monophenols whose chief component is phenol. This distillate then can be recycled to the first stage of reaction as a replacement for phenol, in whole or in part. That is to say, if the distillate from the second product mixture is formed in insufficient quantity to replace all of the phenol, the difference can be made up by the addition of phenol itself. Whatever the case, it is found that the product from the first reaction stage remains rich in cresols when methanol is used as the lower aliphatic alcohol.

It will be apparent to the skilled worker that our invention is capable of many nuances, all of which are intended to be encompassed within our claims. The examples below are merely illustrative and representative of our invention, and should not be interpreted as limiting our invention thereto.

EXAMPLES 1–5

The following description is representative of the experiments performed. To a 300 cc stainless steel stirred autoclave was charged: 25 g phenol; 20 g alkali lignin (Indulin C from Westvaco Corp.); 19.4 g of an aqueous solution containing 2.32 g (0.018 mole) $FeCl_2$, 0.32 g (0.002 mole) $CuSO_4$, and 0.38 g $SnCl_2$ (0.002 mole); 6.2 g $Na_2S.9H_2O$ (0.026 mole); and 10 g water. The reactor was sealed, pressurized three times to 400 psig with nitrogen followed by similar pressurization with hydrogen. Hydrogen then was admitted to a pressure of 100 atm and the reaction mixture maintained at 400° C. for 1 hour. After the mixture was cooled residual gas was measured and analyzed. The product mixture was withdrawn, the reactor was rinsed with toluene, and the toluene wash was combined with the product mixture. The water layer was separated from the combined product and the toluene layer filtered. The solid, which consisted of catalyst particles and insoluble organic solids, was washed with acetone, dried in vacuum at 90° C. for at least 4 hours, weighed, and the percent liquefaction is at least 100[1-(residue/lignin charge)]. The filtrate was dried over sodium sulfate and analyzed by gas chromatography.

Run 1, which duplicates the original Noguchi process and serves as a control, used a charge of 20 g acidified lignin from the Kraft process (Indulin AT from Westvaco Corp.), 50 a phenol, 1.76 g FeS (0.02 mole), 0.19 g CuS (0.002 mole), and 0.30 g $S_nS$ (0.002 mole). Run 2 also utilized acidified lignin to give a strict comparison with the original Noguchi process. In Run 4 there was added 7.9 g methanol, and in Run 5 there was added 3 g methanol. The results are summarized in the following table.

| | LIQUEFACTION OF LIGNIN BY CATALYTIC HYDROGENOLYSIS | | | |
|---|---|---|---|---|
| | Liquefaction, | Yield, % | | |
| Run | % | cresols | $C_6$–$C_8$ phenols | Phenol loss, % |
| 1 | 100 | 22.5 | 38.5 | 1.7 |
| 2 | >87 | 22.5 | 42.0 | 2.2 |
| 3 | >93 | 29.0 | 46.4 | 0.7 (increase) |
| 4 | >79 | 73.0 | 100 | 11.3 |
| 5 | >88 | 45.0 | 59.5 | 3.3 |

Comparison of Runs 1 and 2 show that when acidified lignin is used the Noguchi process and our process afford quite similar yields of cresols and the $C_6$–$C_6$ phenols. Comparison of Runs 2 and 3 show that the use of alkali lignin in our process affords improved yields of both cresols and the $C_6$–$C_8$ phenols generally relative to the use of acidified lignin. Comparison of Runs 3 and 4 show the increase in cresol formation when about 40% methanol is used in the reaction mixture. The increased cresol formation, on a weight basis, can be attributed virtually exclusively to the increased phenol consumption. In Run 5, where the reaction mixture contained only 15% methanol, cresol and $C_6$–$C_8$ phenol yields are substantially increased relative to yields in a methanol-free medium (Run 3) but phenol consumption is drastically decreased relative to Run 4.

EXAMPLE 6

This example shows the production of phenol when lignin tar is used as a solvent in alkali lignin liquefaction. A reaction mixture containing 200 g lignin tars (b.p. greater than about 219° C.), 100 g alkali lignin, 130 g water, 31 g $Na_2S.9H_2O$, and water soluble salts of divalent iron (0.1 mole), copper, and tin (0.01 mole each) in hydrogen at an initial pressure of 60 atm was heated at 400° C. for 2 hours. The mixture was processed as previously described, to afford 250.5 g of an organic phase, of which 33% was phenol and 2.8% were cresols, with 35.9 g of toluene-insoluble solids.

What is claimed is:

1. A method of liquefying lignin from the Kraft process comprising forming in situ a catalystic composition resulting from the addition of a sulfide source to an aqueous solution of divalent iron, and at least one promoter metal selected from the group consisting of copper, tin, silver, chromium, cobalt, nickel, zinc, molybdenum, gallium, and germanium, and reacting a mixture of an aqueous solution of said lignin, phenol, and a lower aliphatic alcohol in the presence of said catalytic composition in a hydrogen atmosphere at a temperature from about 300° to about 450° C. and an initial pressure from about 50 to about 150 atmospheres.

2. The method of claim 1 where the sulfide source is an alkali metal sulfide.

3. The method of claim 2 where the sulfide is sodium sulfide.

4. The method of claim 1 where the amount of each promoter metal present is from about 0.01 to about 0.5 molar proportion relative to iron.

5. The method of claim 1 where the promoter is a combination of divalent copper and divalent tin.

6. The method of claim 5 where the divalent copper and tin are each present in about 0.1 molar proportion relative to iron.

7. The method of claim 1 where the iron is iron(II) sulfide present at a concentration from about 1% to about 10% by weight based on lignin.

8. The method of claim 1 where the alcohol is selected from the group consisting of saturated aliphatic alcohols containing from 1 to about 4 carbon atoms.

9. the method of claim 8 where the alcohol is methanol.

10. The method of claim 1 where the reaction mixture contains from about 1 to about 5 parts by weight phenol relative to lignin.

11. The method of claim 1 where the reaction mixture contains from about 5 to about 100 wt. % alcohol based on lignin.

12. The method of claim 11 where the alcohol is present from about 10 to about 20 wt. %.

13. A method of making cresols from lignin from the Kraft process comprising:
  (a) reacting a mixture of an aqueous solution of the lignin, phenol, and a lower aliphatic alcohol in the presence of a catalytic composition prepared in situ of sulfides of divalent iron and at least one promoter metal selected from the group consisting of copper, tin, silver, chromium, cobalt, nickel, zinc, molybdenum, gallium, and germanium, in a hydrogen atmosphere at a temperature from about 300° to about 450° C. and an initial hydrogen pressure from about 50 to about 150 atmospheres to afford a first product mixture;
  (b) recovering from the first product mixture substantially all material of boiling point less than about 235° C.;
  (c) reacting the remainder fo the first product mixture with an aqueous solution of a lignin salt in the presence of said catalyst compositon in a hydrogen atmosphere at a temperature of 300° to about 450° C. and an initial hydrogen pressure of about 50 to 150 atmospheres to afford a second product mixture;
  (d) recovering fromthe second product mixture substantially all material of boiling point less than about 235° C.; and
  (e) recycling the material of step (d) to step (a) as replacement therein, in whole or in part, for phenol.

14. The method of claim 13 where the iron as iron sulfide is present at a concentration from about 1 to about 10 wt. % based on the lignin present.

15. The method of claim 13 where the alcohol is selected from the group consisting of saturated aliphatic alcohols containing from 1 to about 4 carbon atoms.

16. The method of claim 15 where the alcohol is methanol.

17. The method of claim 13 where the reacton mixture contains from about 5 to about 100 wt. % alcohol based on the lignin present.

18. The method of claim 17 where the alcohol is present at a concentration between about 10 and about 20 wt. %.

19. The method of claim 13 where the promoter is a combination of divalent tin and copper.

20. The method of claim 13 where each promoter metal is present in from 0.01 to about 0.5 molar proportion relative to divalent iron.

21. The method of claim 19 where tin and copper are each present in about 0.1 molar proportion relative to iron.

* * * * *